United States Patent [19]
Schmidt et al.

[11] Patent Number: 5,397,315
[45] Date of Patent: Mar. 14, 1995

[54] APPARATUS FOR ELECTRICALLY CONTROLLING THE DISCHARGE OF URINE FROM A URINE COLLECTION BAG

[75] Inventors: Robert N. Schmidt, Cleveland; Artie M. Dorsey, Grafton, both of Ohio

[73] Assignee: Cleveland Medical Devices, Inc., Cleveland, Ohio

[21] Appl. No.: 231,770

[22] Filed: Apr. 25, 1994

[51] Int. Cl.⁶ .............................................. A61M 1/00
[52] U.S. Cl. ................................................ 604/323
[58] Field of Search .......................... 604/322–325, 604/331; 208/52 R, 61.58 R

[56] References Cited

U.S. PATENT DOCUMENTS

| | | | |
|---|---|---|---|
| 3,931,650 | 1/1976 | Miller | 604/323 |
| 5,092,856 | 3/1992 | Johnston | 604/249 |
| 5,137,102 | 8/1992 | Houston et al. | 180/65.5 |

OTHER PUBLICATIONS

R.D. Equipment Inc. Brochure on Electric Leg Bag Emptier.

Primary Examiner—Jerome L. Kruter
Attorney, Agent, or Firm—Robert N. Schmidt; John Henry Vynalek

[57] ABSTRACT

Apparatus and method for discharging urine from a urine collection bag using an electrically operated valve means connected to the drain tube of the urine collection bag and the electrically operated valve means mounted on a support means, such as a wheelchair, in a manner to be separated from the user's skin and clothing. The electrically operated valve means is controlled by actuating at least two electrical switching means. Upon actuation of the electrical switching means, the electrically operated valve means operates and the urine discharges from the urine collection bag through the drain tube.

1 Claim, 2 Drawing Sheets

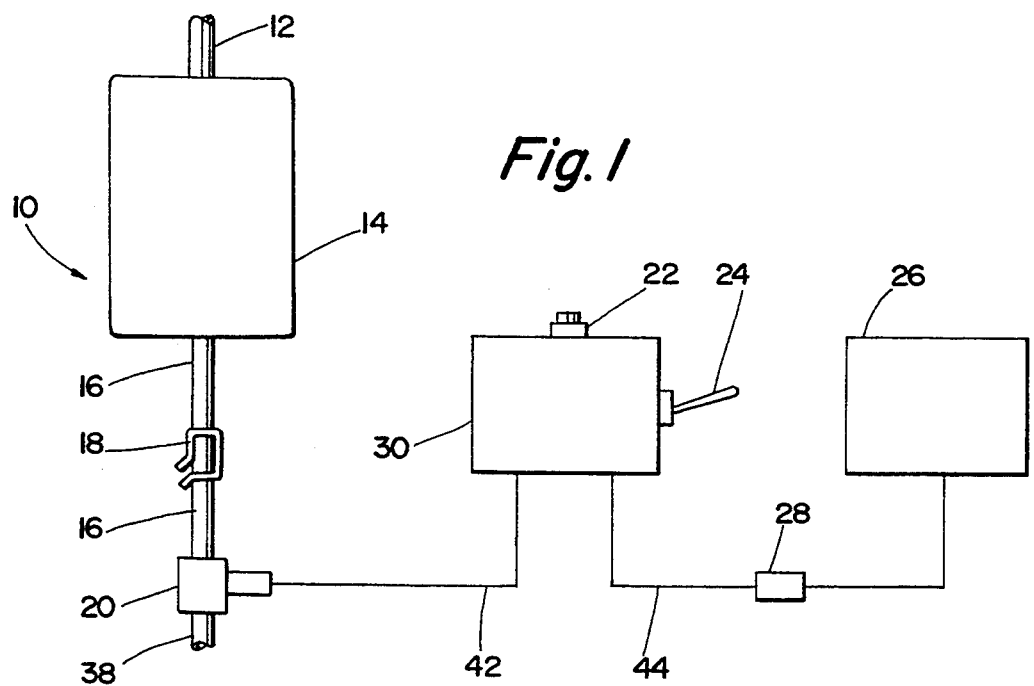
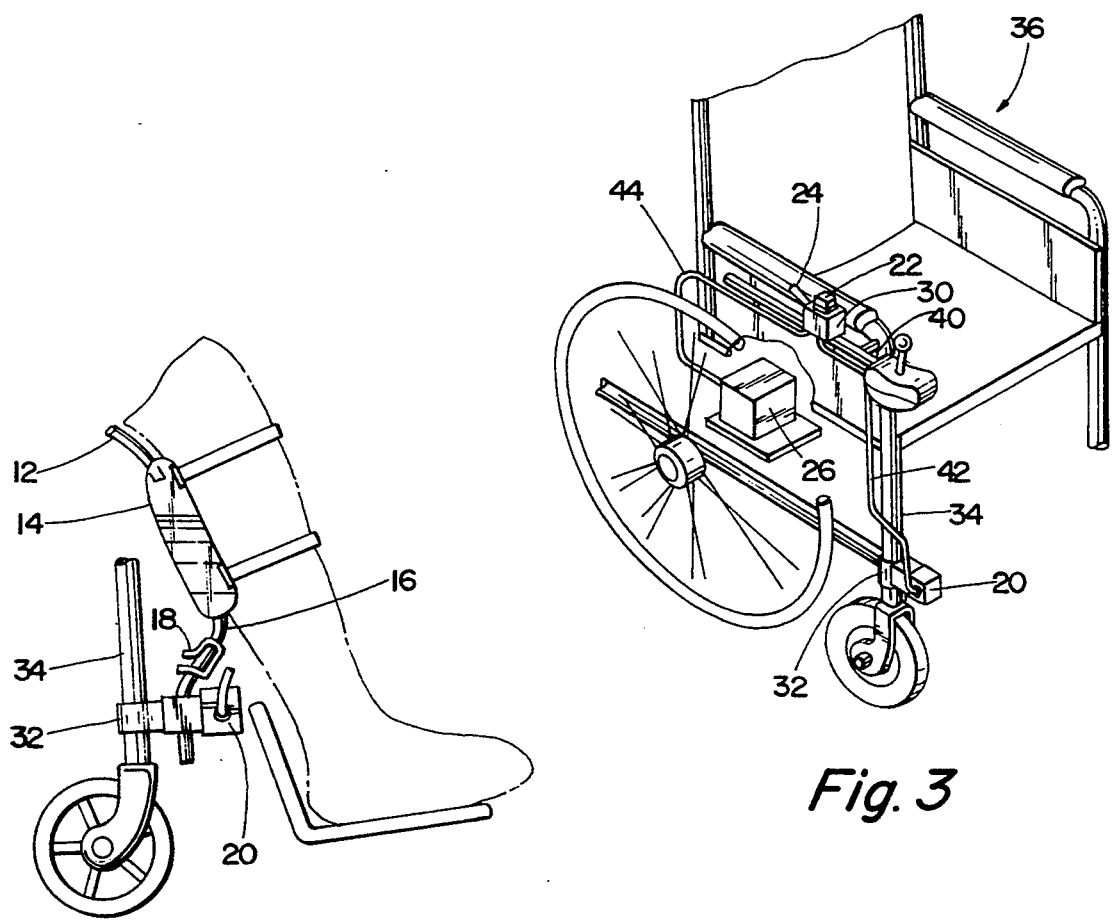
Fig. 1
Fig. 2
Fig. 3

APPARATUS FOR ELECTRICALLY CONTROLLING THE DISCHARGE OF URINE FROM A URINE COLLECTION BAG

BACKGROUND OF THE INVENTION

The present invention generally relates to systems for discharging urine from a urine collection bag and, more particularly, is concerned with apparatus and method for controlling the discharge of urine from a urine collection bag using an electrically operated valve means.

Disabled persons', particularly quadriplegics', ability to control even the most routine activities is greatly restricted due to their disability. This inability can be embarrassing, disconcerting and health threatening when it involves basic bodily functions, like urinating. To urinate quadriplegics must employ some type of externally located urine collection device. Typically, the urine collection device is composed of a urine collection bag connected to the quadriplegic by a catheter or like device. Since the urine collection bag can be discretely concealed on the quadriplegic's body and collects urine until it is intentionally emptied, the quadriplegic can interact in public with a level of comfort and without the fear of an uncontrollable discharge. This level of comfort is not without a limit, though.

Urine collection bags are commonly equipped with a drain tube and require a mechanical clamp, or like means, attached to the drain tube to control the discharge of urine from the urine collection bag. In order to discharge urine from the urine collection bag, the mechanical clamp must be manually opened. Quadriplegics due to their limited ability for movement, are often unable to independently open the mechanical clamp. Accordingly, in order to periodically discharge the urine collection bag, a quadriplegic is required to seek the aid or assistance of another person. This results in the restriction of a quadriplegic's freedom and independence, and embarrassment when such activity needs to occur in non-private surroundings. As an effect of the above-mentioned restriction and embarrassment, quadriplegics with urine collection bags frequently tend to drink less liquid which results in dehydration and subsequent serious physical problems associated therewith.

An apparatus for discharging urine from a urine collection bag utilizing an electrically operated valve is currently available. The electrically operated valve is attached to the drain tube of the urine collection bag at a point in close proximity or in direct contact with the user's leg and clothing. The electrically operated valve is opened by actuating an electrical switch which may be in the form of a toggle switch or a puff switch.

While this apparatus does alleviate the embarrassment involved with another person manually opening a mechanical clamp and does provide for more independent activity for the quadriplegic, its design and operation may result in unintentional discharge of urine, electrical problems such as exposure to live electrical power and burns, and discomfort and tissue damage to the user.

Consequently, a need exists for improvement in electrically controlling the discharge of urine from a urine collection bag which improvement would eliminate the drawbacks associated with such apparatus.

SUMMARY OF THE INVENTION

The present invention provides an apparatus and a method for discharging urine from a urine collection bag designed to satisfy the aforementioned need. The invention embodies a design which assures against inadvertent or unintentional discharge of urine, protects the user from possible burning from electrical devices, eliminates the possibility of exposure to a live electrical power source and provides more comfort for and no tissue damage to the user.

Accordingly, the present invention relates to apparatus and method to discharge urine from a urine collection bag. In one broad aspect the apparatus of the invention comprises a urine collection bag having a drain tube wherein urine is collected in the urine collection bag and discharges through the drain tube; an electrically operated valve means connected to the drain tube wherein the discharge of urine through the drain tube is controlled by the operation of the electrically operated valve means; a support member wherein the electrically operated valve means is mounted independently of the urine collection bag to the support member, a first and second electrical switching means electrically connected to the electrically operated valve means so that both electrical switching means must be actuated in order to operate the electrically operated valve means.

In another aspect, the invention is directed to the method of discharging urine from a urine collection bag comprising the steps of: providing a urine collection bag having a drain tube wherein urine is collected in the urine collection bag and discharges through the drain tube; providing an electrically operated valve means connected to the drain tube; providing a support member wherein the electrically operated valve means is mounted independently of the urine collection bag; providing at least two electrical switching means electrically connected to the electrically operated valve means; actuating at least two electrical switching means to operate the electrically operated valve means and discharge the urine from the urine collection bag.

BRIEF DESCRIPTION OF THE DRAWINGS

Further features of the present invention will become apparent to those skilled in the art to which the present invention relates from reading the following specification with reference to the accompanying drawings in which:

FIG. 1 is a diagram showing the physical connection of a urine collection assembly and the apparatus of the present invention.

FIG. 2 is a detail view showing the mounting of the urine collection bag and electrically operated valve means to a wheelchair.

FIG. 3 is a perspective view showing the mounting of the urine collection assembly to a wheelchair and the apparatus of the present invention.

DESCRIPTION OF THE PREFERRED EMBODIMENT

Figure 2A:
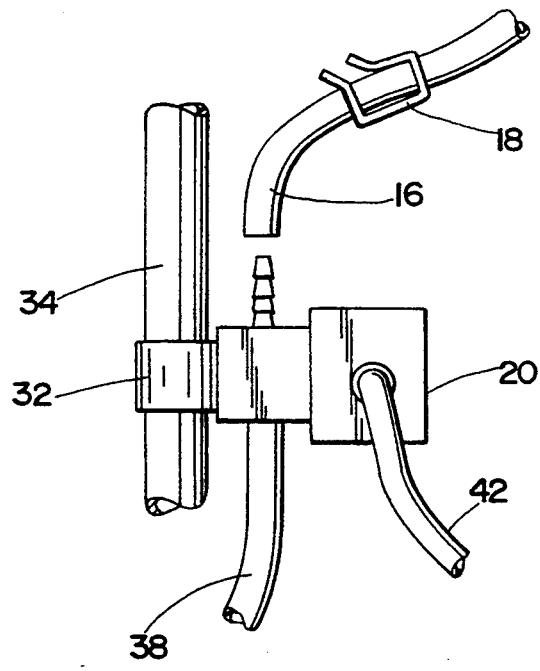
FIG. 2A is a detail view showing the connection of the drain tube to the electrically operated valve means.

While in the preferred embodiment a wheelchair environment is used, it is understood that the present invention can be used with any other environment involving the use of a urine collection bag. Referring now to the drawings and more particularly FIG. 1, there is first shown as a portion of the figure a conventional urine collection assembly 10, comprising a catheter outlet tubing 12 and urine collection bag 14, drain tube 16, and mechanical clamp 18. In the conventional urine collection assembly 10, the mechanical clamp 18 is the only means for controlling the discharge of urine from the urine collection bag 14.

Also as shown in FIG. 1, an electrically operated valve means 20 is connected to the drain tube 16 at a location downstream from the mechanical clamp 18. A discharge tube 38 is connected to the electrically operated valve means 20. The electrically operated valve means 20 is controlled by at least two electrical switching means 22, 24 and powered by an electrical power source 26. The electrically operated valve means 20, the electrical switching means 22, 24 and the electrical power source 26 are interconnected by two 2-conductor wires 42, 44. Circuit protection means 28 is also provided and wired on one of the conductors of interconnecting wire 44. Advantageously, the electrical switching means 24 is a maintained action electrical switching means and the electrical switching means 22 is a momentary action electrical switching means. Preferred forms for the electrical switching means 22, 24 are a toggle switch 24 and a push button switch 22. Electrical switching means 22, 24 will generally be mounted on an enclosure 30. Advantageously, the electrical switching means 22, 24 should be capable of being operated by the paralyzed hand of the quadriplegic.

A push button switch 22 which produces an audible noise e.g. a click, when actuated and deactuated, providing auditory feedback to the quadriplegic user that the switch contact is made or broken is most preferred. Advantageously, the circuit protection means 28 is a fuse. The circuit protection means 28 can also be a circuit breaker. In addition, in the event the circuit protection means 28 is a circuit breaker it is contemplated that it can be used as a maintained action electrical switching means 24. It is preferred that the electrically operated valve means 20 is a solenoid valve. The electric power source 26 can be any a.c. or d.c. power source, but in wheelchair environments will usually be the wheelchair battery.

Referring now to FIG. 2, the detail of mounting the urine collection bag 14 and the electrically operated valve means 20 is shown. The electrically operated valve means 20 is provided with a valve attaching means 32 to allow it to be mounted independently from the urine collection bag 14 on a support member 34 e.g., a part of the frame of a wheelchair 36. (FIG. 3) The electrically operated valve means 20 is mounted lower than the urine collection bag 14 to allow urine in the urine collection bag 14 to flow by gravity to the electrically operated valve means 20. In FIG. 2, the urine collection bag 14 is shown attached to the leg of the user, but it may be attached to any part of the support member 34 or elsewhere provided that the electrically operated valve means 20 is lower than the urine collection bag 14. The drain tube 16 is routed down through the mechanical clamp 18 to the electrically operated valve means 20 which is mounted to allow separation between it and the user to reduce contact with the user's skin or clothing. This separation reduces the probability of burning the user's skin if an electrical short occurs, continuously actuating and overheating the electrically operated valve means 20. Along with the electrically operated valve means 20, a discharge tube 38 may be attached to the electrically operated valve means 20 to direct the flow of urine out of the electrically operated valve means 20. It is desirable that the electrically operated valve means 20 is mounted on the drain tube 16 in such a location so that the mechanical clamp 18 is positioned between the urine collection bag 14 and the electrically operated valve means 20.

Referring now to FIG. 2A, the detail of the connection of the drain tube 16 to the electrically operated valve means 20 is shown. The drain tube 16 is releasably attached to the electrically operated valve means 20. The drain tube 16 may be attached to the electrically operated valve means 20 using a quick coupling and disconnection means or the like. When the user intends to leave the environment in which the present invention is used, the user actuates the electrical switching means 22, 24 which operates the electrically operated valve means 20 to discharge any urine in the urine collection bag 14, drain any remaining urine in the drain tube 16 and the electrically operated valve means 20, itself. The user then closes the mechanical clamp 18 to isolate the electrically operated valve means 20 from the flow of urine. The drain tube 16 is then detached from the electrically operated valve means 20. The urine collection bag 14, drain tube 16 and mechanical clamp 18 can then remain with the user while the electrically operated valve means 20 remains with the environment in which the present invention is used, e.g., a wheelchair 36. (FIG. 3) This eliminates the need to electrically disconnect the electrically operated valve means 20 thus reducing the potential for exposure to live electrical power.

Referring now to FIG. 3 showing the location and mounting of the apparatus of the present invention in a wheelchair 36 environment. The enclosure 30 containing at least two electrical switching means 22, 24 is mounted to a supporting means, like a control bar 40 of a wheelchair 36. The enclosure 30 is mounted in a manner to be within reach of and easily accessible to the person using the wheelchair 36. The electrically operated valve means 20 is mounted with attaching means 32 on support member 34 which is part of the frame of the wheelchair 36 at a point close to the bottom of the wheelchair 36. Interconnecting wire 42 is routed along the frame of the wheelchair 36 between the electrically operated valve means 20 and the enclosure 30. Interconnecting wire 44 is routed along the frame of the wheelchair 36 between the enclosure 30 and the circuit protection means 28 and electrical power source 26.

Figure 4:
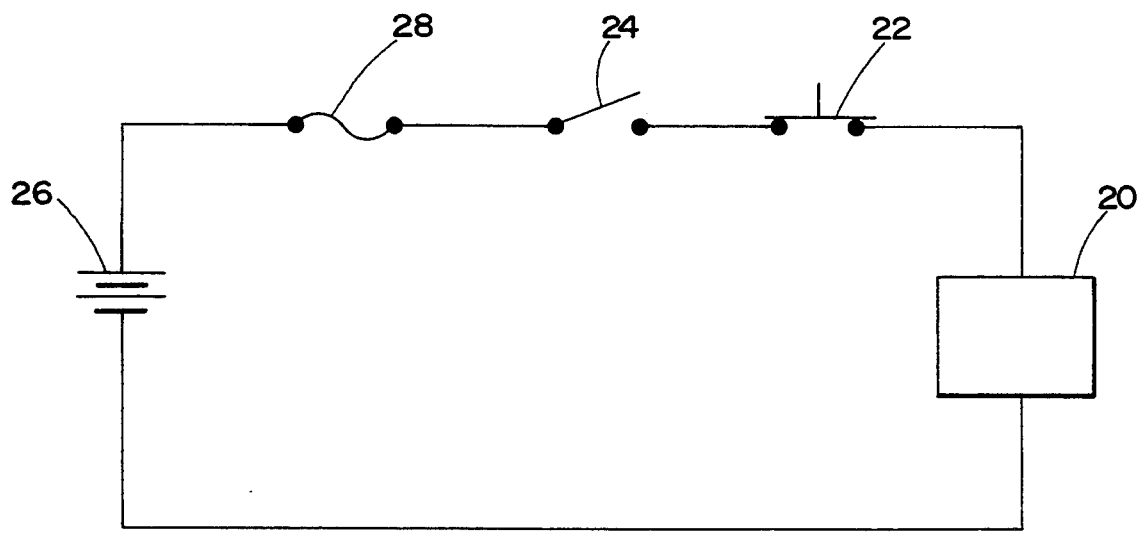
FIG. 4 is a schematic diagram illustrating the electrical connection of the electrical power source, circuit protection means, electrical switching means, and the electrically operated valve means.

Referring now to FIG. 4 a schematic diagram of the preferred embodiment is shown. The circuit protection means 28 is electrically connected in series between the positive terminal of the electrical power source 26 and the electrical switching means 22, 24. The electrical switching means 22, 24 are electrically connected in series with the electrically operated valve means 20. The electrically operated valve means 20 is electrically connected to the negative terminal of the electrical power source ;26. While FIG. 4 illustrates one preferred electrical arrangement of the invention, it should be understood that other electrical arrangements are possible.

Referring again to FIG. 1 the method for discharging urine from a urine collection bag 14, using electrical power involves actuating all of the electrical switching means 22, 24. To assure against unintended operation, the electrical switching means 22, 24 are actuated in a sequential manner. The maintained action electrical switching means 24 is actuated first remaining in its actuated state while the momentary action electrical switching means 22 is then actuated. This closes the electrical circuit between the electrical power source 26 and the electrically operated valve means 20, allowing electrical current to flow to the electrically operated valve means 20 from the electrical power source 26, thereby opening the electrically operated valve means 20 and permitting urine from the urine collection bag 14 to discharge through the drain tube 16 and the discharge tube 38.

While there has been shown and described only one embodiment in accordance with the present invention, it is understood that the same is not limited thereto but is susceptible to numerous changes and modifications as known to those skilled in the art, therefore the invention is not to be limited to the details shown and described herein, but it is intended to cover all such changes and modifications as are encompassed by the scope of the appended claims.

What is claimed is:

1. An apparatus for discharging urine from a urine collection bag comprising:

a urine collection bag having a drain tube wherein urine is collected in said urine collection bag and discharges through said drain tube; and an electrically operated valve means connected to said drain tube wherein the discharge of urine through said drain tube is controlled by the operation of said electrically operated valve means; and a support mender wherein said electrically operated valve means is mounted independently of said urine collection bag to said support member; and first and second electrical switching means connected to said electrically operated valve means so that both electrical switching means must be actuated in order to operate said electrically operated valve means, wherein said first electrical switching means is a maintained action electrical switching means and wherein said second electrical switching means is a momentary action electrical switching means and wherein said momentary action electrical switching means produces an audible noise when actuated and deactuated.

* * * * *